(12) United States Patent
Bazargan et al.

(10) Patent No.: US 8,181,849 B2
(45) Date of Patent: May 22, 2012

(54) COLOR DETECTION SYSTEM FOR DETECTING RESERVOIR PRESENCE AND CONTENT IN DEVICE

(75) Inventors: Afshin Bazargan, Simi Valley, CA (US); Pablo Vazquez, Granada Hills, CA (US); Salman Monirabbasi, Los Angeles, CA (US); Paul H. Kovelman, Simi Valley, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 666 days.

(21) Appl. No.: 12/346,730

(22) Filed: Dec. 30, 2008

(65) Prior Publication Data
US 2010/0164727 A1    Jul. 1, 2010

(51) Int. Cl.
*G06F 17/00* (2006.01)
(52) U.S. Cl. ................... 235/375; 235/462.01
(58) Field of Classification Search ............. 235/375, 235/462.01; 604/66, 151, 260
See application file for complete search history.

(56) References Cited

U.S. PATENT DOCUMENTS

| | | | |
|---|---|---|---|
| 2006/0224128 A1* | 10/2006 | Lurvey et al. | 604/250 |
| 2008/0033360 A1* | 2/2008 | Evans et al. | 604/151 |
| 2008/0249470 A1* | 10/2008 | Malave et al. | 604/151 |

FOREIGN PATENT DOCUMENTS

| | | |
|---|---|---|
| EP | 1872814 A1 | 1/2008 |
| GB | 2006678 A | 5/1979 |
| JP | 2003-220136 A | 8/2003 |
| WO | 2005032449 A1 | 4/2005 |
| WO | 2006084464 A1 | 8/2006 |
| WO | 2006129301 A2 | 12/2006 |
| WO | 2006129301 A3 | 12/2006 |
| WO | 2008146021 A1 | 12/2008 |
| WO | 2008150715 A1 | 12/2008 |

OTHER PUBLICATIONS

Invitation to Pay Additional Fees with Partial International Search Report for PCT/US2009/068789 mailed May 10, 2010.
PCT International Search Report and Written Opinion for PCT/US2009/068789 mailed Aug. 11, 2010.

* cited by examiner

*Primary Examiner* — Ahshik Kim
(74) *Attorney, Agent, or Firm* — Medtronic MiniMed, Inc.

(57) ABSTRACT

A system for identifying a reservoir used with a fluid delivery device. The system includes a reservoir comprising a housing for holding fluid and a colored marking located on a surface of the housing. A fluid delivery device includes a compartment for receiving and operatively coupling with the reservoir. A light source shines light on the colored marking of the reservoir. A color sensor detects wavelengths reflected and/or refracted from the colored marking due to the light shined on the colored marking. A processor of the delivery device determines a color of the colored marking from the detected wavelengths and ascertains information related to the reservoir or the fluid in the reservoir corresponding to the determined color, wherein the processor operates the fluid delivery device according to the ascertained information, wherein the information may include a reservoir type and/or medication type.

12 Claims, 10 Drawing Sheets

COLOR DETECTION SYSTEM FOR DETECTING RESERVOIR PRESENCE AND CONTENT IN DEVICE

FIELD OF THE INVENTION

Embodiments of the present invention relate to a system for detecting the presence and content of a reservoir used in a fluid delivery device by detecting a colored marking located on the reservoir.

BACKGROUND OF THE INVENTION

Infusion devices and systems have become relatively prevalent in the medical field for use in delivering or dispensing prescribed medication such as insulin to a patient. In one form, such devices comprise a transportable, pocket-size pump housing capable of receiving a reservoir of medication for administration to the patient through an associated catheter or infusion set.

Infusion devices have significant advantages over traditional medication delivery methods because of their precision, consistency, and versatility. Patients are able to set exact dosage amounts and generally benefit from receiving medication from pumps during physical activity or other occasions that would otherwise not easily be suited for doing so. As a result, infusion pumps have effectively reduced the restrictions that a diabetic patient's medical needs place upon him allowing the patient to live a more active and fulfilling lifestyle.

Generally, medication reservoirs have been used with the infusion devices to deliver medication to the patient. Typically, the medication reservoir is operatively inserted in, or attached to, the infusion device. A plunger is then actuated to force medication out of the reservoir, and deliver the medication via a tube to an insertion site on the patient.

Prior to methods being developed for detecting the presence or identifying the contents of a medication reservoir, a user manually checked if the reservoir was attached or inserted into a delivery device. The user was also responsible for ensuring that the medication or dosage was the correct one to administer. These steps are critical because a lack of the reservoir in the infusion device prevents the patient from receiving vital medication. Moreover, administration of an incorrect medication or dosage can lead to patient injury or death. Generally, the user must know what type of medication is being administered because there are often different dosing requirements for different concentrations of the same medication.

To overcome the drawbacks concerning what type of medication is contained in the reservoir, information related to the medication was printed on the exterior of the reservoir. However, this method suffers because the user must still view the printing on the reservoir and understand the information presented.

Other systems for providing information about the reservoir to the delivery device have been developed but also suffer from various disadvantages. For example, a delivery system includes mechanical switches that are manipulated by the reservoir when the reservoir is inserted into the device to provide information about the reservoir. However, such a device is disadvantageous because inclusion of the mechanical switches undesirably increases the size of the delivery device. Moreover, the switches must be accessible to the reservoir, and thus, it is difficult to maintain a waterproof device housing to protect the internal components of the delivery device from any fluids escaping from the reservoir or otherwise entering the device. The system is also susceptible to error when the reservoir's orientation in the device is not in an ideal position with respect to the switches.

In yet another example, a medication delivery system includes a bar code reader mounted in the delivery device. The bar code reader is used in conjunction with a medication reservoir having a bar code on its surface. The bar code provides information related to the medication contained in the reservoir, such as type, volume, dosage, etc. Accordingly, when the reservoir is inserted into the delivery device, the bar code reader in the device reads the bar code on the reservoir, and uses the information obtained from the bar code to operate the device, or provide the information to the user on a device display.

However, such a system suffers from several drawbacks. For example, bar code readers need to be a certain distance away from the bar code to properly read the bar code. Consequently, devices accommodating bar code readers are larger in size, which is undesirable to users. Moreover, the bar codes on the reservoir require precise positioning in the device to be properly read by the bar code reader. Hence, device reliability and accuracy are easily lowered if the reservoir is moved slightly away from its ideal position in the device.

SUMMARY OF THE INVENTION

Embodiments of the present invention are directed to a system for detecting the presence and content of a reservoir operatively coupled to a delivery device by detecting a colored marking located on the reservoir.

Additional features and advantages of embodiments of the invention will be set forth in the description which follows, and in part will be apparent from the description, or may be learned by practice of embodiments of the invention. The objectives and other advantages of embodiments of the invention will be realized and attained by the structure particularly pointed out in the written description and claims hereof as well as the appended drawings.

To achieve these and other advantages and in accordance with the purpose of embodiments of the present invention, as embodied and broadly described, the present invention is embodied in a reservoir for use with a fluid delivery device for delivering fluid into a body from the reservoir, the reservoir including a housing for holding fluid, and at least one colored marking located on a surface of the housing for providing information related to the reservoir or the fluid in the reservoir to the fluid delivery device. In particular, the housing is adapted to operatively couple with the delivery device, and a color of the at least one colored marking is adapted to be determined by the fluid delivery device to provide the information related to the reservoir or the reservoir fluid in the reservoir corresponding to the determined color.

In some embodiments, the information includes at least one of a medication type, a medication expiration date, an amount of medication contained in the reservoir, a maker of the medication, a medication concentration, a medication dosage, a reservoir size, and a reservoir material. The information may be stored in a memory of the delivery device.

In one embodiment, the at least one colored marking may include a plurality of colored markings. In another embodiment, the color of the at least one colored marking may be adapted to change to indicate information related to the reservoir or the fluid in the reservoir.

In yet another embodiment, a fluid delivery device for delivering fluid into a body of a patient from a reservoir containing the fluid and having at least one colored marking that encircles a housing of the reservoir includes a compartment for receiving the reservoir, and the fluid delivery device operatively couples with the housing of the reservoir to deliver the fluid into the body of the patient from the reservoir. The fluid delivery device also includes a light source for shining light on the at least one colored marking of the reservoir, a color sensor for detecting wavelengths reflected and/or refracted from the at least one colored marking due to the light shined on the at least one colored marking, and a processor operatively coupled to the color sensor for determining the color of the at least one colored marking from the detected wavelengths and ascertaining information related to the reservoir or the fluid in the reservoir corresponding to the determined color.

The processor may ascertain the information related to the reservoir or the reservoir fluid in the reservoir by acquiring information stored in a memory of the fluid delivery device corresponding to the determined color. The processor may also operate the delivery device according to the ascertained information. The processor may communicate to other processors in the device. Further, if the processor determines a lack of any color or detect the color of reservoir housing, the processor may determine that no reservoir has been received into the fluid delivery device. Moreover, the processor may determine a position of the reservoir in the fluid delivery device based on the determined color. In an additional embodiment, the fluid delivery device may include a second color sensor for detecting wavelengths reflected and/or refracted from the at least one colored marking due to the light shined on the at least one colored marking.

In another embodiment of the present invention, a fluid delivery system for delivering fluid into a body of a patient includes a reservoir and a fluid delivery device. The reservoir includes a housing for holding the fluid and at least one colored marking located on a surface of the housing for providing information related to the reservoir or the fluid in the reservoir. The fluid delivery device includes a compartment for receiving the reservoir, and the fluid delivery device operatively couples with the housing of the reservoir to deliver the fluid into the body of the patient from the reservoir. The delivery device also includes a light source for shining light on the at least one colored marking of the reservoir and a color sensor for detecting wavelengths reflected and/or refracted from the at least one colored marking due to the light shined on the at least one colored marking. The delivery device further includes a processor operatively coupled to the color sensor for determining the color of the at least one colored marking from the detected wavelengths and ascertaining information related to the reservoir or the reservoir fluid in the reservoir corresponding to the determined color.

In a further embodiment of the present invention, a characteristic monitor system for monitoring a characteristic of a user comprises a remote device, a sensor set supporting a sensor for producing a signal indicative of the characteristic of the user, at least one colored marking located on a surface of the sensor set for providing information related to the sensor set or the characteristic of the user, and a transmitter coupled to the sensor set for processing signals from the sensor set and transmitting the processed signals to the remote device, wherein the remote device utilizes the received processed signals to determine the characteristic of the user. The transmitter comprises a light source for shining light on the at least one colored marking of the sensor set, a color sensor for detecting wavelengths reflected and/or refracted from the at least one colored marking due to the light shined on the at least one colored marking, and a processor operatively coupled to the color sensor for determining a color of the at least one colored marking from the detected wavelengths and ascertaining information related to the sensor set or the monitored characteristic corresponding to the determined color.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. Features, elements, and aspects of the invention that are referenced by the same numerals in different figures represent the same, equivalent, or similar features, elements, or aspects in accordance with one or more embodiments.

DETAILED DESCRIPTION OF THE PREFERRED EMBODIMENTS

Figure 1A:
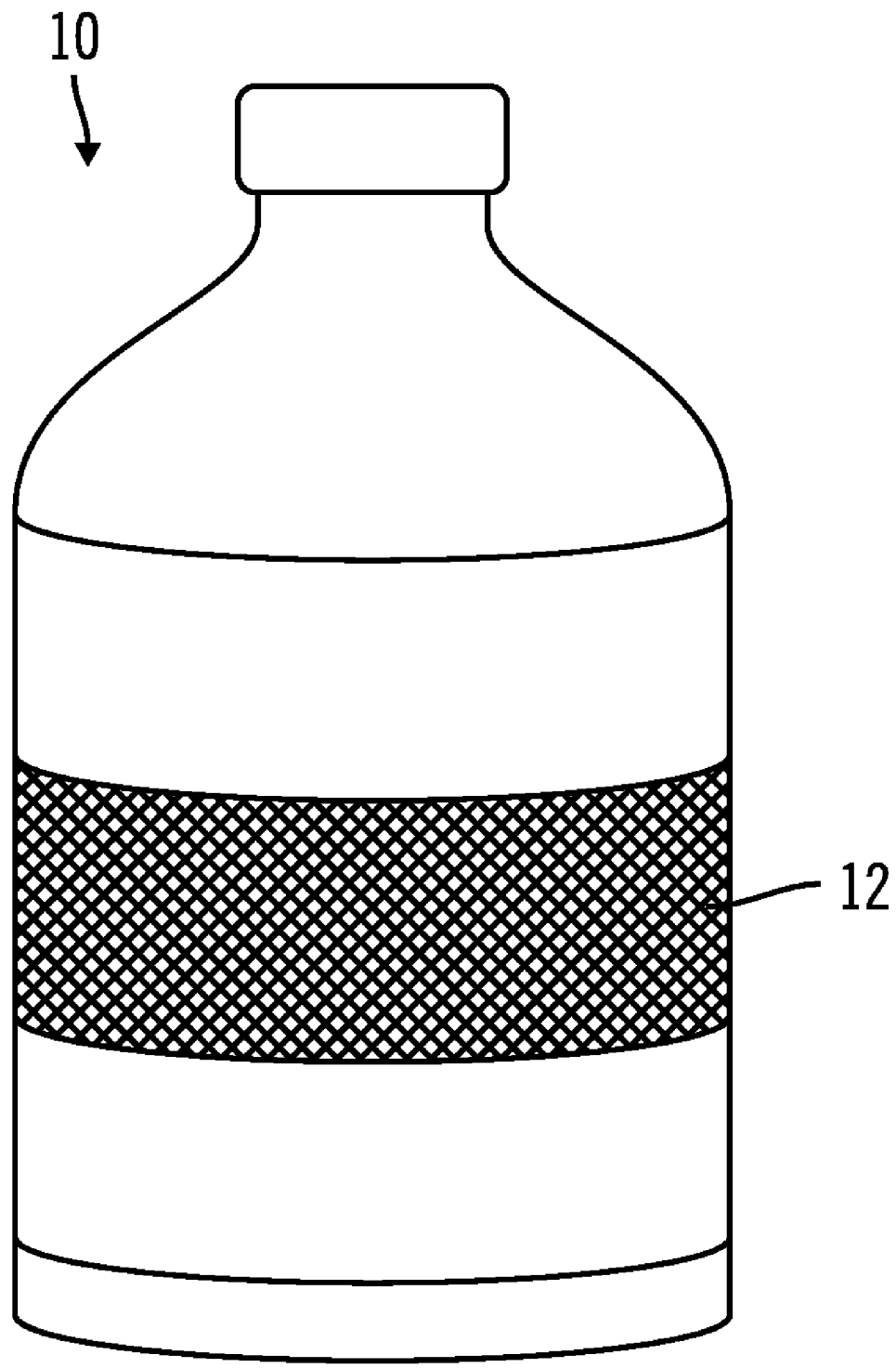
FIG. 1A illustrates an exemplary fluid reservoir in accordance with an embodiment of the present invention.

Embodiments of the present invention relate to detecting the presence and/or determining information about a reservoir operatively coupled to a fluid delivery device based on a colored marking located on the reservoir.

As shown in the drawings for purposes of illustration, embodiments of the invention include a fluid reservoir or reservoir that is used in conjunction with a fluid delivery device for delivering fluid contained in the reservoir to a patient. In particular embodiments, the fluid reservoir is used to deliver medication, such as insulin, into the patient's body. In further embodiments, the fluid reservoir may be used to deliver medical substances, such as vitamins, hormones, vaccines, antibiotics or other medications, or other liquid substances, such as dyes, tracers or the like. The fluid reservoir includes a colored marking on a surface of the reservoir. When sensed by the delivery device, the colored marking allows the delivery device to detect the reservoir's presence, as well as determine characteristics of the reservoir and the fluid contained in the reservoir. In alternative embodiments, the color may be formed inside the reservoir material (as a separate insert, different colored material formed during the molding, a label between layers in a multi-layer wall of a reservoir) as an opaque or translucent section. In other alternatives, the color may be adhered to the interior of the reservoir. In particular embodiments, the reservoir has a circular cross-section forming a generally cylindrical container. However, in alternative embodiments, the cross-section of the reservoir is oval, square, rectangular, triangular, polygonal (which may include sharp or rounded corners), or the like.

Embodiments of the present invention may be implemented in an external infusion device including a housing worn on the exterior of the patient's body generally of the type described in U.S. Pat. Nos. 4,562,751; 4,678,408; 4,685,903; 5,080,653; 5,097,122; 5,505,709; 6,248,093; 6,362,591; 6,554,798; 6,555,986; and 6,752,787, which are specifically incorporated by reference herein in their entirety. The colored marking may be located on the fluid reservoir or other medical fluid container used in conjunction with the external infusion device. When the colored marking is sensed by the infusion device, it may indicate information including, but not limited to, medication type (e.g. type of insulin), expiration date, amount of medication contained in the reservoir, maker of the medication, medication dosage, proper insertion of the reservoir, reservoir size, reservoir material (e.g. Topas®, glass, etc.) or the like.

In further embodiments, the infusion device may include separate durable and disposable housing portions that selectively engage and disengage from each other and may be of the type generally described in U.S. application Ser. No. 11/211,095 filed Aug. 23, 2005 and entitled "Infusion Device and Method with Disposable Portion," U.S. application Ser. No. 11/588,875 filed Oct. 27, 2006 and entitled "Systems and Methods Allowing for Reservoir Filling and Infusion Medium Delivery," U.S. application Ser. No. 11/515,225 filed Sep. 1, 2006 and entitled "Infusion Medium Delivery Device and Method with Drive Device for Driving Plunger in Reservoir," U.S. application Ser. No. 11/588,847 filed Oct. 27, 2006 and entitled "Infusion Medium Delivery Device and Method with Compressible or Curved Reservoir or Conduit," U.S. application Ser. No. 11/646,000 filed Dec. 26, 2006 and entitled "Infusion Medium Delivery System, Device and Method with Needle Inserter and Needle Inserter Device and Method," and U.S. application Ser. No. 11/589,323 filed Oct. 27, 2006 and entitled "Infusion Pumps and Methods and Delivery Devices and Methods with Same," all of which are incorporated by reference herein in their entirety. The colored marking may be located on the fluid reservoir used in conjunction with the infusion device. When the colored marking is sensed by the durable portion of the infusion device, it may indicate information including, but not limited to, medication type (e.g. type of insulin), expiration date, amount of medication contained in the reservoir, maker of the medication, medication dosage, proper insertion of the reservoir, reservoir size, reservoir material (e.g. Topas®, glass, etc.) or the like. Alternatively, the colored marking may be located on the disposable portion of the infusion device to indicate such information as well as the usage life of the disposable portion. In further alternative embodiments, the colored marking may be located on the durable portion of the infusion device, and may indicate information such as the usage life of the durable portion.

Other embodiments of the present invention may be implemented in sensors (such as glucose, lactate, bacterial, viral, ph, oxygen, or the like), sensing systems, senor monitors and/or an infusion system that receives data from a sensor inserted into a patient's body as generally described in U.S. patent application Ser. No. 10/867,529 entitled "System for Providing Blood Glucose Measurements to an Infusion Device" filed on Oct. 14, 2004, or a characteristic monitoring system that receives continuous data from a sensor inserted into a patient's body as generally described in U.S. Pat. Nos. 6,248,067; 6,424,847; and 6,895,263; and U.S. patent application Ser. No. 09/377,472, filed Aug. 19, 1999 and entitled "Telemetered Characteristic Monitor System And Method Of Using The Same," and U.S. patent application Ser. No. 11/322,568, filed Dec. 30, 2005 and entitled "Telemetered Characteristic Monitor System And Method Of Using The Same," all of which are incorporated by reference herein in their entirety. Such systems typically include a characteristic monitor coupled to a sensor set inserted into the patient's body to determine levels of a characteristic in the patient's body, such as blood glucose levels. The colored marking may be located on the sensor set. When the colored marking is sensed by the portion coupling the sensor set to the characteristic monitor (i.e., cable connected between the sensor set and the monitor, transmitter connected to the sensor set that wirelessly transmits data to the monitor), it may indicate information such as the usage life of the sensor (e.g., 3 days, 6 days), the analyte being sensed (e.g, glucose, lactate, bacterial, viral, ph, oxygen, or the like), calibration data, alarm thresholds, lot number, or the like.

An infusion device according to embodiments of the present invention may include a housing to enclose a drive system, a fluid containment assembly, and a power supply. The device's drive system generally includes a small motor (DC, stepper, solenoid, piezoelectric, piston drive, peristaltic pump, shape memory alloy driven or other type) and drive train components such as gears, screws and levers that act in concert to convert rotational motor motion to translational displacement of a piston in a fluid reservoir. In some embodiments, the drive system may use gas, or other types of pressure systems that induce displacement of the piston in the fluid reservoir. The fluid containment assembly may include the reservoir, flexible tubing, and a catheter or infusion set that transports the fluid or medication from the infusion device to the body of the user. Alternatively, the fluid containment assembly may include the reservoir, and fluid or medication may be delivered directly from the reservoir through the infusion device (without the necessity of an infusion set and/or tubing) to the body of the user. The device's electronic system may include programmable controls for regulating the motor, as well as for setting desired dosage intervals over a certain period of time.

FIG. 1A illustrates an exemplary medication reservoir in accordance with a particular embodiment of the present invention. Referring to FIG. 1A, a reservoir 10 includes a colored marking 12. The reservoir 10 is made of a suitable glass or plastic material. However, in alternative embodiments, the reservoir 10 may be made out of other materials, such as composites, metals, ceramics, Topas® or the like. The marking 12 may be a colored band encircling the reservoir 10, and may be placed on a surface of the reservoir 10 by means of a painted mark, printing, spraying, molding, adhered sticker, or the like. Alternatively, the marking 12 may be a single patch of color on one area of the reservoir, or a series of small patches extending around the circumference of the reservoir. The marking 12 may also be formed as part of a label that includes information such as text, trademarks, volume, identification and lot number. This facilitates the marking 12 to be attached to the reservoir 10 in a single operation with the other information.

The colored marking 12 is not limited to colors in the visible spectrum. In particular embodiments, the marking 12 may be of an infrared and/or ultraviolet color, the wavelengths of which are detectable by a color sensor used in connection with embodiments of the present invention. Use of colors outside of the visible spectrum allows for greater information-providing capabilities and/or prevents information from being visible to the user.

Figure 1B:
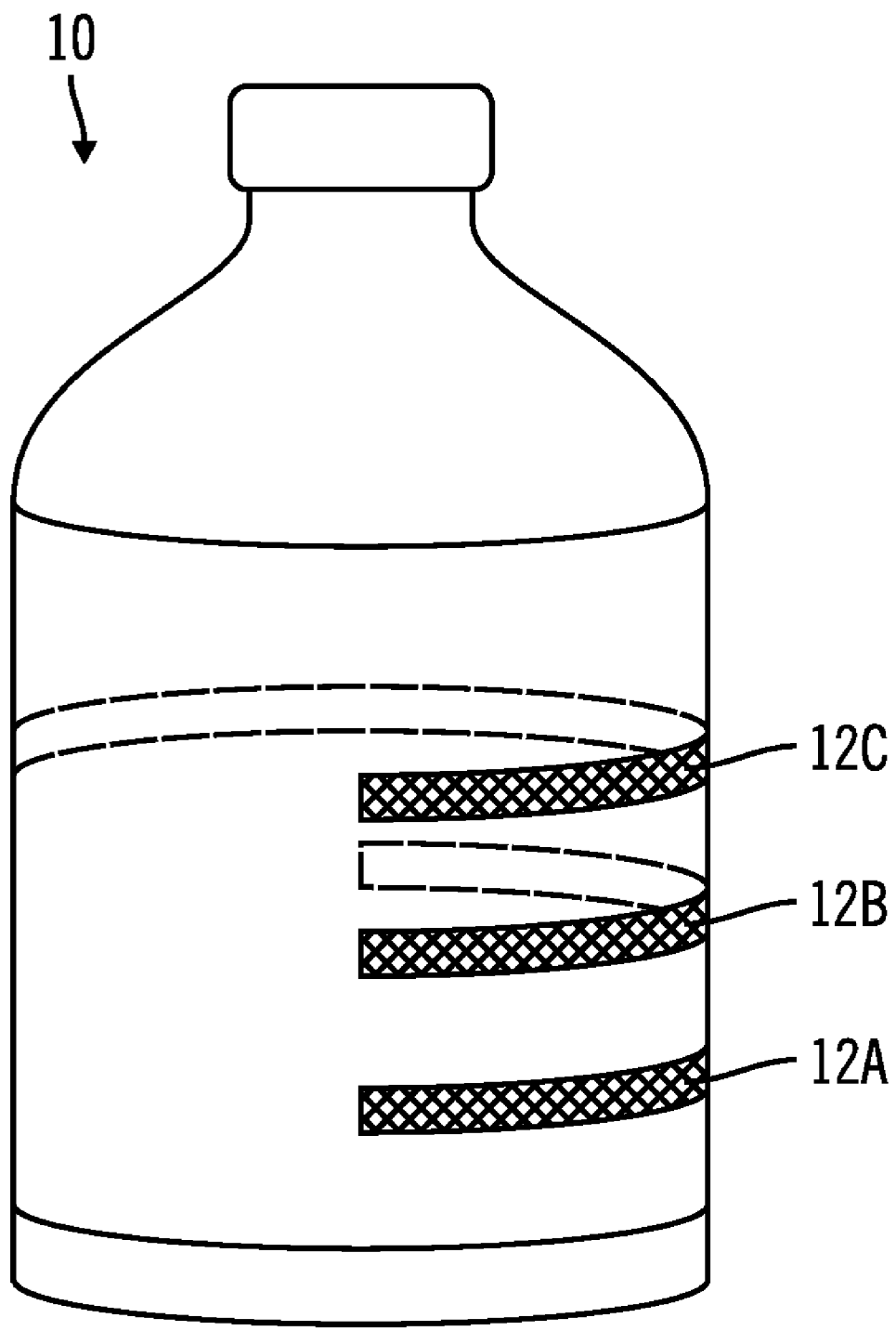
FIG. 1B illustrates an exemplary fluid reservoir in accordance with an embodiment of the present invention having colored bands which extend partially around the reservoir.

Alternatively, the marking 12 may be a colored band that extends partially around the reservoir 10, as shown in FIG. 1B. When the reservoir 10 is inserted into a fluid delivery device, such as the device illustrated in FIG. 2, the device may actuate a plunger to force medication out of the reservoir 10 to be delivered to a patient via an infusion set or the like that is adhered to the patient. In further alternatives, the color band may only cover certain angular segments of the reservoir, such as 180 degrees, 90 degrees, 45 degrees, 30 degrees, 15 degrees or other suitable amount, with the selection being based upon the width of color band required, orientation features of the reservoir, size of a color sensor or the like. For illustrative purposes only, colored markings 12A, 12B and 12C are shown in FIG. 1B to respectively cover angular segments of 90 degrees, 180 degrees and 270 degrees of the reservoir 10. Although FIG. 1B shows multiple colored bands extending around the reservoir at respectively different angular segments, it is contemplated that the multiple colored bands may also extend equally around the reservoir to cover equal angular segments. Moreover, the angular segments may be of any angle, and are therefore not limited to the angles shown in FIG. 1B.

In particular embodiments, when the colored band covers a certain angular segment of the reservoir, a window 50 (shown in FIG. 2A) of the fluid delivery device may be sized large enough such that a color sensor of the device is able to detect at least a portion of the colored band through the window 50 regardless of a distance between the color sensor and the reservoir inserted in the delivery device. Alternatively, when the colored band covers a certain angular segment of the reservoir, the reservoir may be configured such that it is inserted in the delivery device with a particular orientation so that a smaller portion of the colored band is visible to the color sensor through the window 50, and therefore makes it unnecessary for the colored band to extend all the way around the surface of the reservoir. Additionally, if the colored band covers an angular segment of at least 180 degrees, and if the liquid in the reservoir is clear enough to accurately allow colors to be transmitted through, a label for attaching to the reservoir may be formed with color on both sides of the label. This allows the colored marking to be detected by the color sensor regardless of the reservoir's orientation in the delivery device.

Figure 1C:
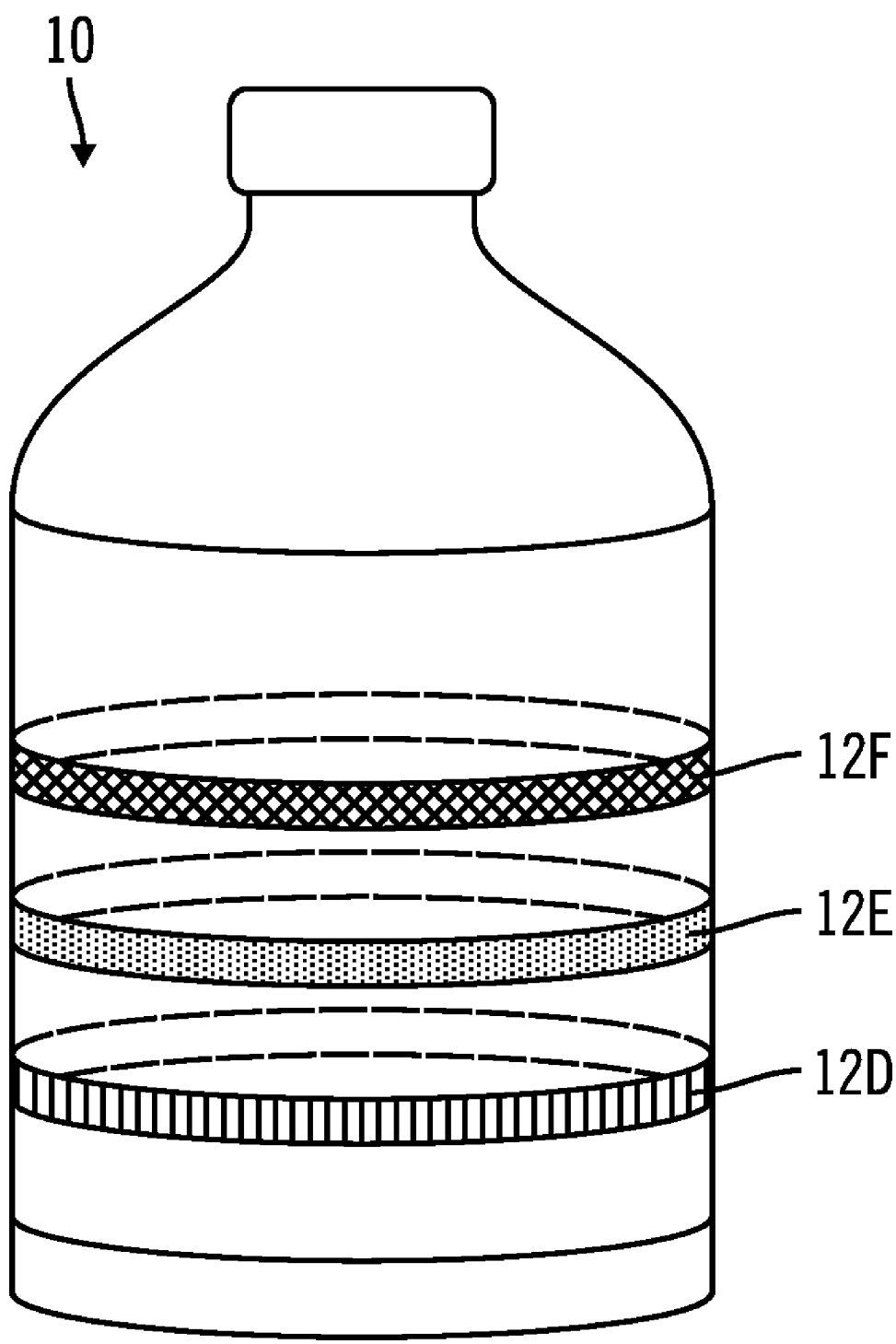
FIG. 1C illustrates an exemplary fluid reservoir in accordance with an embodiment of the present invention having different colored bands.

In alternative embodiments, the reservoir 10 may include a plurality of colored markings. As shown in FIG. 1C, different colored bands 12D, 12E and 12F may encircle the reservoir 10. The colored bands may be separated from each other or adjoin each other according to need, wherein the need may depend on a sensitivity and size of a color sensor, a size of the reservoir or the like. The different colored bands may also partially extend around the reservoir 10, as shown in FIG. 1B.

Figure 1D:
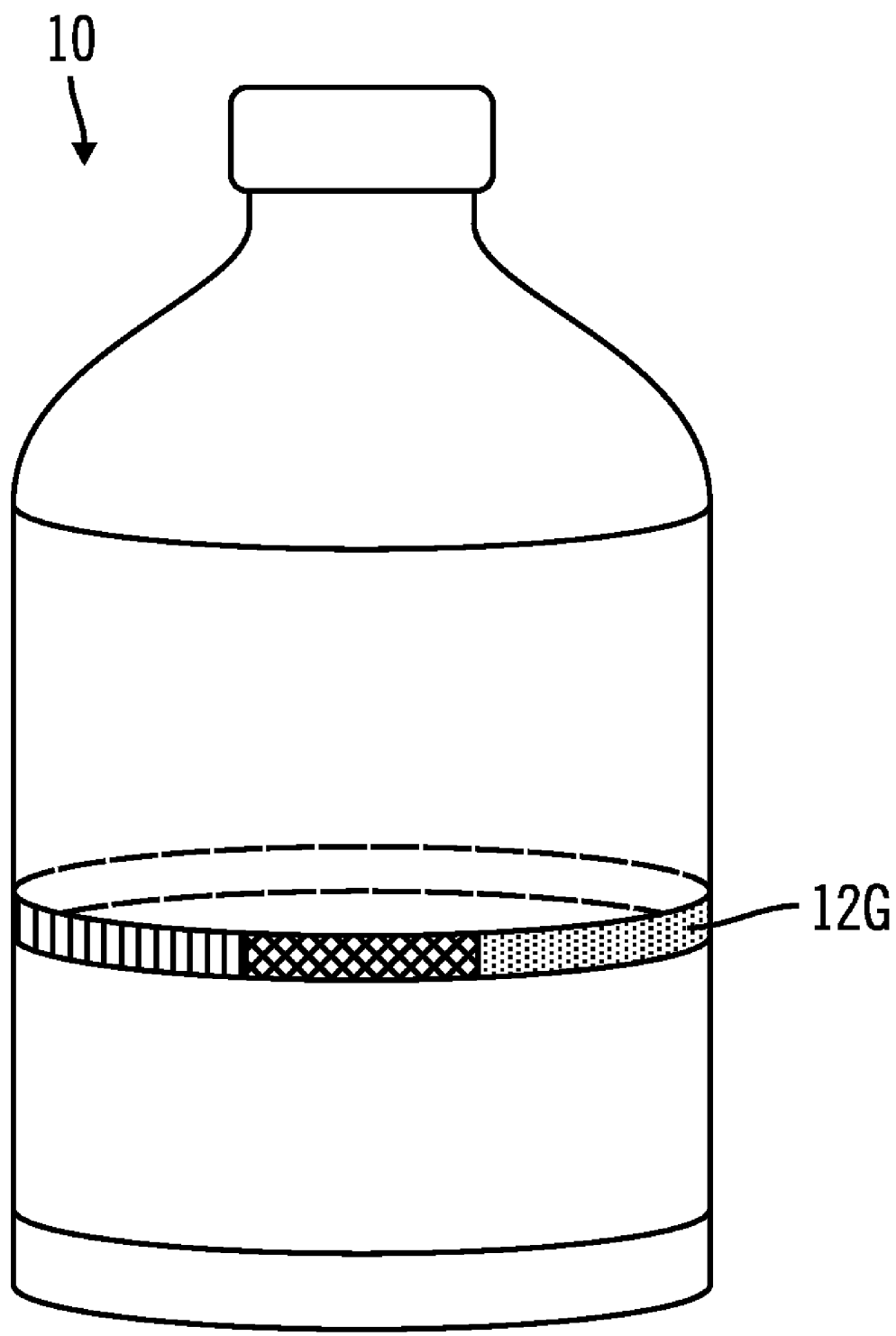
FIG. 1D illustrates an exemplary fluid reservoir in accordance with an embodiment of the present invention having a band with different colors.

As shown in FIG. 1D, a colored band 12G comprising a plurality of colors may be located on the reservoir 10. Different colored regions may alternate around the band 12G. In a particular embodiment, the different colored regions may be small in size such that a single color sensor of a fluid delivery device is able to detect multiple color regions. Alternatively, the different colored regions may be spaced apart from each other such that a plurality of color sensors of the delivery device may be used to respectively detect the spaced-apart colored regions. The plurality of color sensors may be co-located or separated in the delivery device.

Figure 2A:
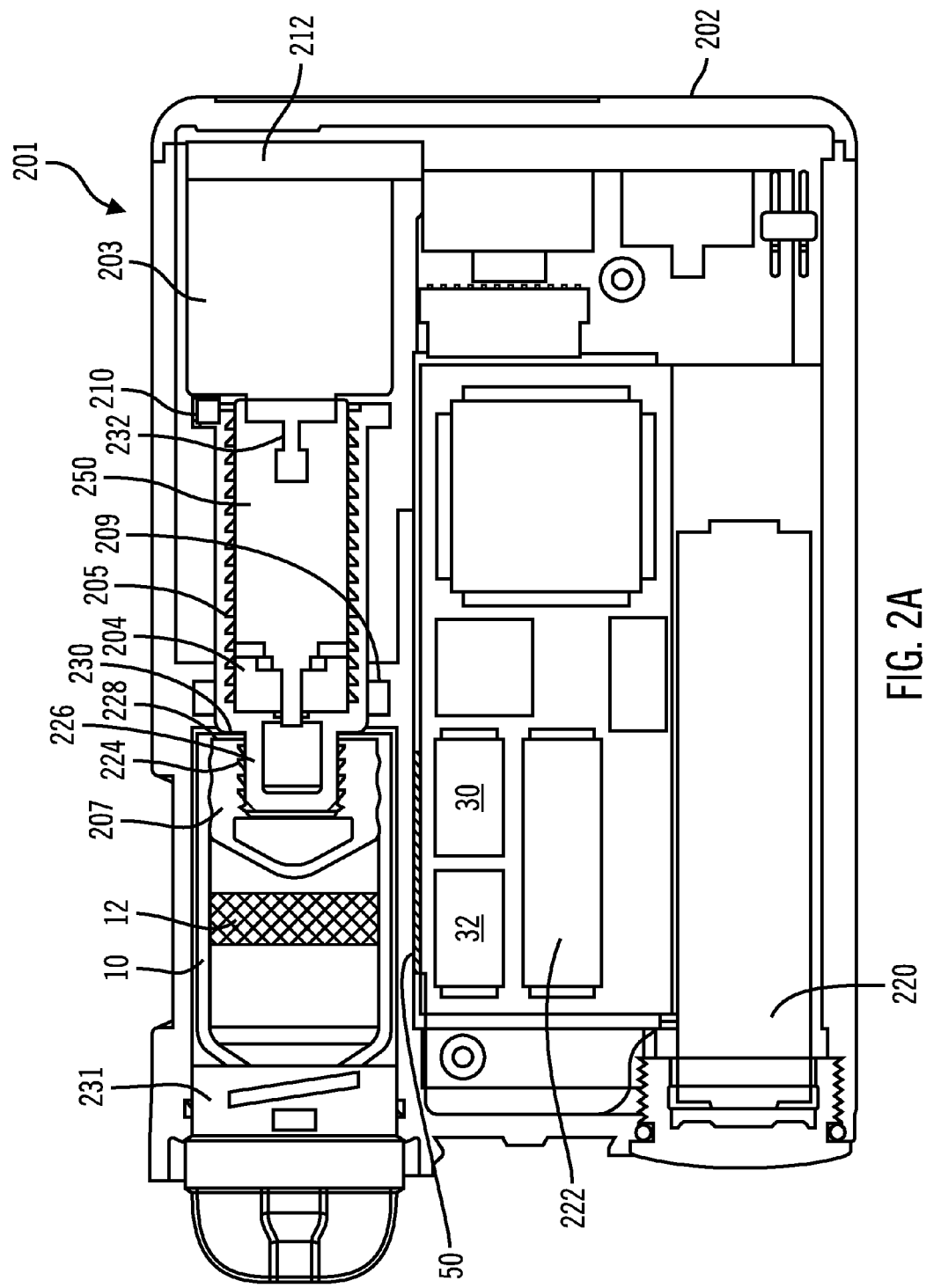
FIG. 2A illustrates a side plan, cut-away view of an exemplary fluid delivery device in accordance with an embodiment of the invention.

FIG. 2A illustrates a front plan, cut-away view of an exemplary fluid delivery device according to a particular embodiment of the invention, in which a device 201, containing a lower section 202 for a power supply 220 and electronic control circuitry (microprocessor) 222, accommodates a driving device, such as a motor 203 (e.g., a solenoid, stepper or DC motor), a first drive member, such as an externally threaded drive gear or screw 204, a second drive member, such as an internally threaded plunger gear or slide 205, and a removable reservoir 10. The reservoir 10 may include a plunger or piston 207 with O-rings or integral raised ridges for forming a water and air tight seal. The reservoir 10 is inserted into a compartment in the device 201 and secured into the device 201 with a connector 231 which also serves as the interface between the reservoir 10 and an infusion set adhered to the patient (not shown). In particular embodiments, the reservoir piston 207 is coupled to a plunger slide 205 by a releasable coupler. In the illustrated embodiment, the coupler includes a female portion 224 which receives a male portion 226 carried by the plunger slide 205. The female portion 224 is positioned at the end face 228 of the piston 207 and includes a threaded cavity which engages the threads of a male screw extending from the end 230 of the plunger slide 205.

While particular embodiments of the present invention are directed to disposable, pre-filled reservoirs 10, alternative embodiments may use user-filled, refillable, refurbished, or the like reservoirs 10. The reservoir 10 can be pre-filled with insulin (or other drug or fluid) and inserted into the fluid delivery device. Alternatively, the reservoir 10 may be filled by the patient using an adapter handle (not shown) attached to the piston 207 on the reservoir 10. After the reservoir 10 is filled, the handle is removed (such as by unscrewing the handle) so that the reservoir 10 can be placed into the fluid delivery device.

Referring to FIG. 2A, as the drive shaft 232 of the motor 203 rotates, the drive screw 204 drives the plunger slide 205 directly to obtain the axial displacement against the reservoir piston 207 to deliver the predetermined amount of medication or fluid. A gear box 250 couples the drive screw 204 to the drive shaft 232 of the motor 203. When using a DC or stepper motor, the motor can be rapidly rewound when the reservoir is emptied or as programmed by the user. A sealing device, such as a seal 209, is in contact with the plunger slide 205, thus allowing it to move axially while maintaining a water resistant barrier between the cavity holding the reservoir 10 and the motor 203. This prevents fluids and other contaminants from entering the drive system.

An anti-rotation key 210 is affixed to the plunger slide 205 and is sized to fit within a groove (not shown) axially disposed in the device 201. This arrangement serves to prevent motor and plunger slide rotation which might otherwise result from the torque generated by the motor 203 in the event that the friction of the seal 209 is not sufficient alone to prevent rotation.

The motor 203 is a motor, such as a DC or stepper motor, and is journal mounted in the device 201 by a mounting system 212. The mounting system 212 can be useful in aiding motor startup.

The device 201 includes a light source 30 and a color sensor 32. Preferably, the light source 30 may be a single white light emitting diode (LED) or a plurality of individual color LEDs. The color sensor 32 may be a color sensing chip, photodiode or photo integrated circuit (photo IC). In one embodiment, a photo IC sensitive to red ($\lambda$=615 nm), green ($\lambda$=540 nm) and blue ($\lambda$=465 nm) regions of the color spectrum may be used. In particular embodiments, detected signals may be serially output as 12-bit digital data. Thus, the photo IC may comprise three 12-bit digital registers allowing simultaneous measurement of three colors (red, green and blue). In alternative embodiments, smaller or larger digital data bit sizes may be used, depending on the resolution or number of colors that needs to be detected.

Figure 2B:
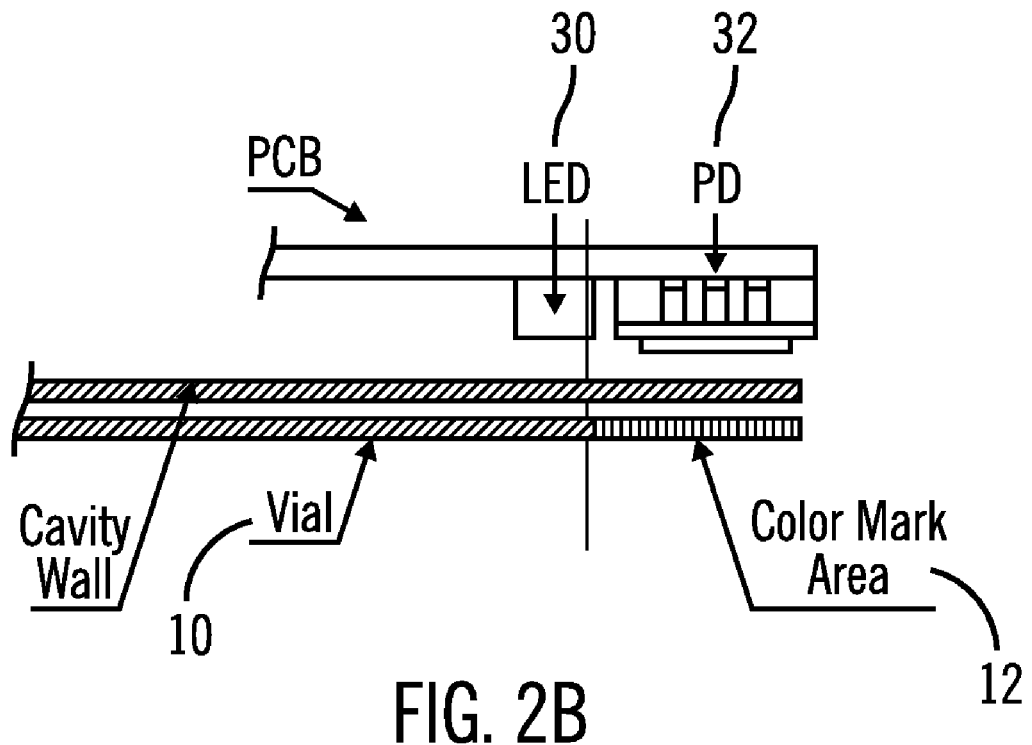
FIGS. 2B and 2C illustrate alternative embodiments of an exemplary fluid delivery device in accordance with an embodiment of the invention.
Figure 2C:
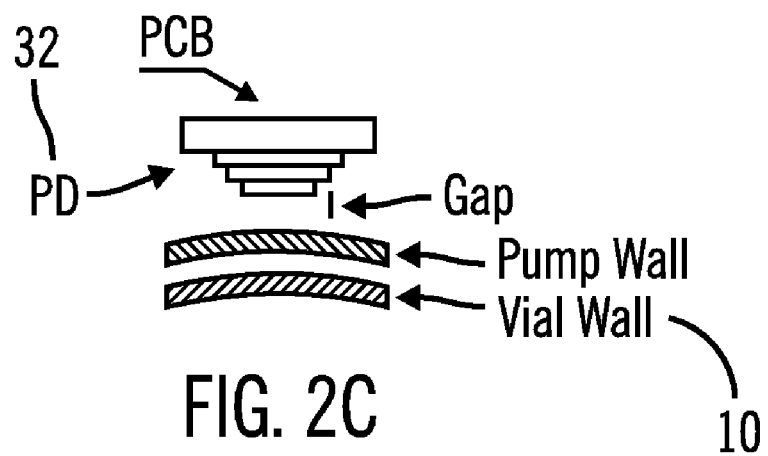

The colored marking 12 on the reservoir 10, and the light source 30 and color sensor 32 of the device 201, are purposefully placed such that when the reservoir 10 is inserted into the device 201, the light source 30 is able to shine light on the colored marking 12 while the sensor 32 detects wavelengths reflected and/or refracted from the marking 12. In particular, the colored marking 12 surrounds the reservoir 10 so that the light source 30 is able to shine light on the colored marking 12, and the sensor 32 is able to detect the resulting wavelengths, regardless of the reservoir's orientation in the device. As shown in FIGS. 2B and 2C, the light source 30 and color sensor 32 are operatively coupled to a printed circuit board (PCB) so as to be electrically coupled with other electrical components of the device 201.

In particular embodiments, the inserted reservoir 10 is separately encased within the device 201 to form a fluid-tight seal around the reservoir 10 to protect the reservoir fluid from contaminants, and to protect device components, such as the light source 30 and sensor 32, from contacting any fluid escaping from the reservoir 10. Accordingly, a window 50 may be formed on a wall separating the reservoir 10 from the light source 30 and sensor 32, as shown in FIG. 2A. This allows the light source 30 to shine light on the colored marking 12 of the reservoir 10 and the sensor 32 to detect the reflected and/or refracted wavelengths from the reservoir 10 while being protected from any harmful fluid. Preferably, the window 50 is made of a polycarbonate material. Moreover, the sensor 32 is capable of detecting the wavelengths through the window 50 regardless of the window being distorted or dirty.

In another embodiment, the window 50 is not used. Rather, the wall separating the reservoir 10 from the light source 30 and sensor 32 is a translucent material of the device 201, which allows light to pass through. In this embodiment, the source 30 is able to shine light onto the marking 12, and the sensor 32 is capable of detecting the reflected wavelengths through the translucent wall to detect the color of the marking 12. In alternative embodiments, other case colored materials may be used, as long as they do not interfere with the ability to detect and determine the color.

The device 201 further includes the microprocessor 222 operatively coupled to the sensor 32 via the PCB shown in FIGS. 2B and 2C, for example. In particular, the microprocessor 222 is programmed with control algorithms to receive output data from the sensor 32 to determine a specific color of the marking 12. For instance, the control algorithms used for detecting the color of the marking 12 when utilizing the above-stated translucent material may be different from the control algorithms used when a clear window is utilized.

Additionally, in particular embodiments, the fluid delivery device 201 has an opaque housing, although in alternative embodiments, the housing may be translucent. The control algorithms used for detecting the color of the marking 12 when the housing is opaque may be different from the control algorithms used when the housing is translucent.

In one embodiment, different colored markings on the reservoir 10 correspond to different medications or medication concentrations, respectively. For example, the color green may correspond to U100 insulin, the color red may correspond to U200 insulin, etc. Accordingly, if the microprocessor 222 determines that the colored marking 12 is green, it can then ascertain the medication contained in the reservoir (i.e. U100 insulin). Upon confirming that U100 insulin is the appropriate medication to deliver, the microprocessor can then operate the device 201 to properly deliver the medication to the patient.

In an alternative embodiment, in lieu of or in addition to a colored marking 12 placed on the reservoir 10, color may be added to the medication itself for purposes of direct identification of the medication by the color sensor 32. Accordingly, embodiments of the present invention described herein with respect to the colored marking 12 are also applicable to colored medication within the reservoir 10.

It is contemplated that any number of colors may be used in accordance with embodiments of the present invention to arbitrarily correspond to a respective medication. Moreover, the embodiments of the present invention are not limited to colors in the visible spectrum. It is contemplated that the marking 12 may also be of an infrared color, the wavelengths of which are detectable by the sensor 32.

In other embodiments, different colored markings on the reservoir 10 may indicate other information such as medication type (e.g. type of insulin), expiration date, amount of medication contained in the reservoir, maker of the medication, medication dosage, proper insertion of the reservoir, reservoir size, reservoir material (e.g. Topas®, glass, etc.) or the like. Thus, upon the microprocessor 222 ascertaining this information, the microprocessor 222 may operate the device 201 according to the information.

In particular embodiments, the relationship between an arbitrary color and corresponding information (e.g., medication type, reservoir size, etc.) is previously known by the device 201 and may be stored in a memory (not shown) of the device 201. The device memory may be preloaded with such information during manufacture of the device. Alternatively, the user may download such information onto the device memory from an external source.

In one embodiment, information deduced from the colored marking may be communicated to a user/patient via a display of the device 201. For example, when the colored marking of the reservoir 10 is detected by the sensor 32, the control algorithms of the device 201 may first deduce the type of medication contained in the reservoir, and convey this information to the user. The user is then able to visually confirm whether the currently connected reservoir contains the correct medication to receive. The information may also be communicated to other devices such as a controller or bedside monitor.

In another embodiment, the information may also be used by the device 201 to improve performance. For example, instead of the user visually confirming the correct medication on the device display, the control algorithms may automatically deduce that the currently connected reservoir contains the incorrect medication, and subsequently notify the user/patient of the error via an alarm, for example, and/or automatically stop delivery of the medication. In another example, in the event that the correct medication is present in the reservoir, the control algorithms may automatically operate the device to deliver the medication according to predetermined delivery parameters related to the determined color and/or the medication. Accordingly, depending on implementation, when the specific color of the marking 12 is determined, different control algorithms of the device 201 may be driven according to the determined color to perform different device functions. For example, the algorithms for detecting an occlusion in the device 201 may be varied depending on the medication type indicated by the colored marking 12. If the colored marking 12 indicates that the reservoir 10 contains a lower insulin concentration (e.g., U50, U100), the occlusion sensitivity may be lower than if the colored marking 12 indicates that the reservoir 10 contains a higher insulin concentration (e.g., U200, U400).

In one embodiment, when the sensor 32 does not detect a color within a certain amount of time, the control algorithms recognize a global lack of any reservoir in the device 201. Accordingly, the device 201 initiates a safety check to inform the user/patient of the missing reservoir and may prompt the user/patient to insert a reservoir, or otherwise investigate the reason for why no reservoir is detected. Alternatively, the control algorithms can determine the lack of a reservoir in the device 201 when the sensor 32 detects a color of the device compartment for receiving the reservoir.

Figure 3:
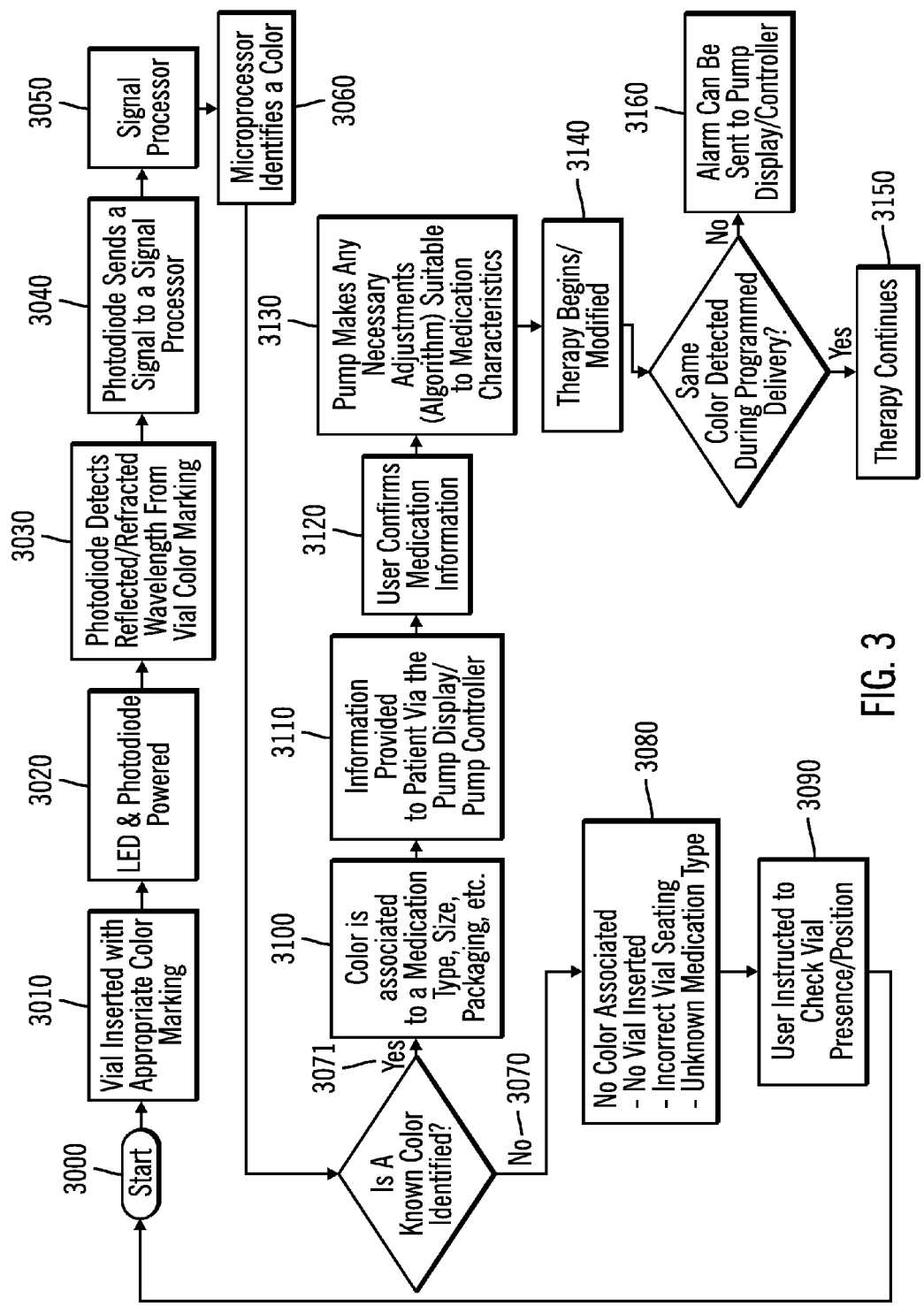
FIG. 3 illustrates a method of operation of a fluid delivery system in accordance with embodiments of the present invention.

FIG. 3 illustrates a method of operation of a fluid delivery system in accordance with embodiments of the present invention. Referring to FIG. 3, a user inserts a reservoir 10 (e.g., vial containing medication to be delivered to the user) having a colored marking 12 into a device 201 (3010). Once the reservoir 10 is inserted, a light source 30 (e.g. LED) and a color sensor 32 (e.g. photodiode) are powered (3020). As the light source 30 shines light onto the colored marking 12, wavelengths reflected and/or refracted from the colored marking 12 are detected by the color sensor 32 (3030). The color sensor 32 then sends a signal representing detected wavelength values to a signal processor (3050), wherefrom a microprocessor 222 attempts to determine a color of the colored marking 12 on the inserted reservoir 10 (3060).

If no color is detected, or if an identified color is new to the processor (3070), the processor may determine that no reservoir is inserted, the reservoir is incorrectly inserted or the reservoir contains an unknown medication type, for example (3080). Accordingly, the device 201 may then prompt the user to perform a safety or corrective action (3090). For example, the user may be instructed to check for the reservoir's presence in the device 201, or check that the reservoir is properly positioned in the device.

If an identified color of the reservoir is previously known to the processor (3071), the processor determines that the color is associated with information related to the reservoir or fluid in the reservoir (3100). The information may include a medication type, a medication expiration date, an amount of medication contained in the reservoir, a maker of the medication, a medication dosage, a reservoir size, a reservoir material, or a medication concentration. The information may be provided to the user via a device display or device controller (3110), wherein the user may confirm the medication information (3120).

Once the user confirms the medication to be delivered, the device 201 may make appropriate delivery adjustments according to the characteristics of the medication (3130) and deliver the medication accordingly (3140). During delivery, the device 201 may check whether the detected color is the same as the color detected during programmed delivery. If so, then the medication delivery continues (3150). However, if the detected color is not the same, then an alarm may be triggered to notify the user of the discrepancy (3160).

In accordance with embodiments of the present invention, the control algorithms may gather reference points to account for ambient light, variations in tolerances, and component drifts in the device 201, and thus, promote the reliability and robustness of the device 201. For example, in particular embodiments, the fluid delivery device 201 has an opaque housing, although in alternative embodiments, the housing may be translucent. If the housing is translucent, the control algorithms must account for the ambient light in order to correctly detect the color of the marking 12. Thus, the control algorithms may gather reference points to determine the amount of ambient light and accordingly adjust to detect the color of the marking 12.

In other embodiments of the present invention, the colored marking 12 may be placed on structures other than the reservoir 10. For example, the colored marking may be placed on the connector 231 connecting the reservoir 10 to an infusion set. Accordingly, the device 201 may ascertain information related to the connector 231 or infusion set (e.g., tubing length, cannula length, type of infusion set, manufacturer of the infusion set, or the like) when the colored marking is detected by the color sensor 32, or another sensor positioned on the device 201 to detect wavelengths reflected and/or refracted from the colored marking on the connector 231. For instance, if color identified the length of the tubing, cannula length, or the like, the amount of fluid needed for the device to prime the infusion set and tubing could be automatically adjusted. The colored marking may also be placed on other portions of medical devices or accessories attached to the patient, such as tubings, cannulas, or the like for a color sensor of the device 201 to be able to ascertain information related to the respective medical device or accessory. In particular embodiments, a corresponding relationship between a detected color on a specific medical device or accessory and information related to the specific medical device or accessory is previously known by the device 201 and may be stored in a memory of the device 201.

In other embodiments of the present invention, the colored marking 12 on the reservoir 10 may be manipulated to indicate various types of information to the device 201. For example, in one embodiment, the marking 12 may form a narrow colored band on the reservoir 10. Accordingly, the narrow band may be used to determine whether the reservoir 10 is positioned in the device 201 correctly. Specifically, because the narrow band poses as a smaller target for the light source 30 to shine light on, if the reservoir 10 is placed in a less-than-ideal position in the device 201, the light may only hit a portion of the colored band, and therefore a weaker signal is produced for the sensor 32 to detect. The weaker signal is indicative of the reservoir being positioned incorrectly in the device.

In another embodiment, the colored marking 12 on the reservoir 10 may be made to purposefully change color to indicate changes in conditions related to the reservoir 10 or reservoir fluid. For example, a controlled fade of the colored marking may be implemented to indicate the age of the reservoir fluid, or whether the reservoir fluid has expired. Furthermore, a change in color of the marking may be used to indicate the age of the reservoir itself. This may be helpful when utilizing reusable/refillable reservoirs. Thus, a user is informed by the color change if a reservoir is too old and unsafe to use. Alternatively, the change in color of the marking may also indicate whether the reservoir or the reservoir fluid has been damaged due to temperature, water or air exposure.

In other embodiments, a plurality of colored markings may be placed on the reservoir 10 to indicate large amounts, or different types, of information to the device 201. Accordingly, the device 201 may have one or more color sensors to detect wavelengths of the plurality of colored markings, and allow the device 201 to ascertain information corresponding to the plurality of colors detected. In one embodiment, use of a second color sensor allows for more accurate color readings. For example, the second color sensor may function to confirm wavelength readings detected by a first color sensor. Accordingly, when determining the color of a colored marking on the reservoir, control algorithms may subtract out colors that are not part of the reservoir by using baseline information known to the device along with the readings from the two color sensors. In particular, use of the second sensor adds minimal size to the device.

The reservoir according to embodiments of the present invention used in conjunction with the light source 30 and light sensor 32 of the device 201 is an improvement over previous systems which utilize alternative methods for providing information about the reservoir to the delivery device. In an example of a previous system, a reservoir having a bar code for use with a delivery device having a bar code reader is employed. The bar code design requires large room in the device because the bar code reader is required to be a certain distance away from the bar code for its reading mechanism to correctly focus on the bar code. Moreover, the bar code design requires the reservoir to be precisely positioned in the device so that the bar code reader can properly align itself with the bar code. Hence, any slight movement of the reservoir away from its ideal position in the device will hinder the bar code reader from accurately reading the bar code and produce unreliable readings. Additionally, the bar code design is susceptible to misreading O-rings of the reservoir as bar codes. Also, the bar code reader has difficulty reading the bar code when a window between the reservoir and the bar code reader is unclear or distorted, or when the bar code itself is unclear or distorted (e.g., debris on the bar code, scratched/damaged bar code label). Furthermore, in the bar code design, more bars are required on the reservoir to indicate more information. However, the need for more bars on the reservoir requires a larger window between the reservoir and the bar code reader to allow the bar code reader to focus on the wider bar code. This is disadvantageous because the larger window increases the size of the device.

Use of color in accordance with the embodiments of the present invention is a more reliable and less cumbersome method of providing information regarding the reservoir, or contents of the reservoir, to the delivery device. It is less demanding for the color sensor 32 to be able to detect wavelengths reflected and/or refracted from the marking 12 on the reservoir 10 than it is for a bar code reader to read a bar code. The color sensor 32 does not require as much space between itself and the reservoir 10. Thus, less room is required in the delivery device 201 of the present invention, and therefore smaller devices may be manufactured. Moreover, in the present embodiments, the reservoir 10 does not require precise positioning in the device 201 because the color sensor 32 is able to detect wavelengths reflected and/or refracted from the marking 12 surrounding the reservoir 10 even when reservoir positioning is less than ideal. Additionally, the color sensor 32 is able to detect wavelengths through an unclear or distorted window. Also, because only the color of the marking 12 is being informed to the color sensor 32, a small window size is adequate, and therefore reduces the size of the device.

Figure 4A:
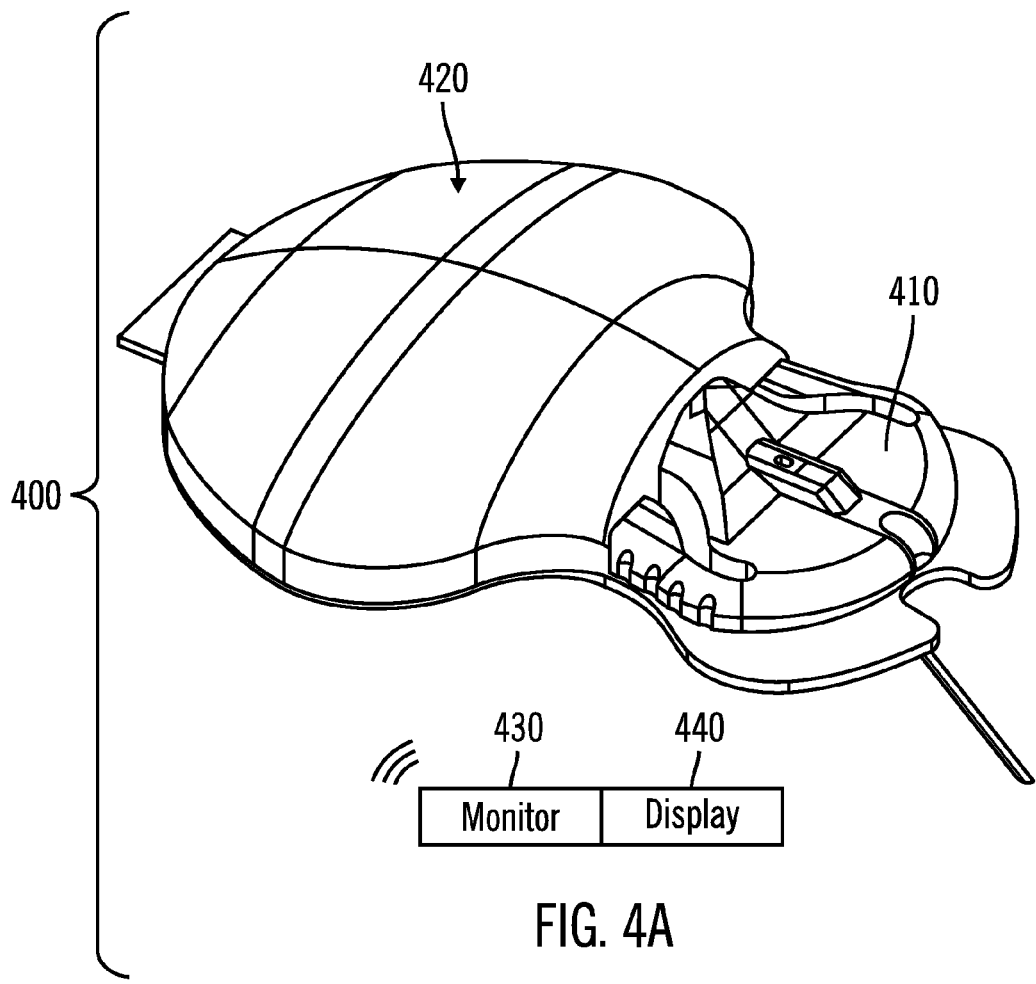
FIGS. 4A and 4B illustrate a characteristic sensor system having a subcutaneous sensor insertion set and a telemetered characteristic monitor transmitter in accordance with an embodiment of the present invention.
Figure 4B:
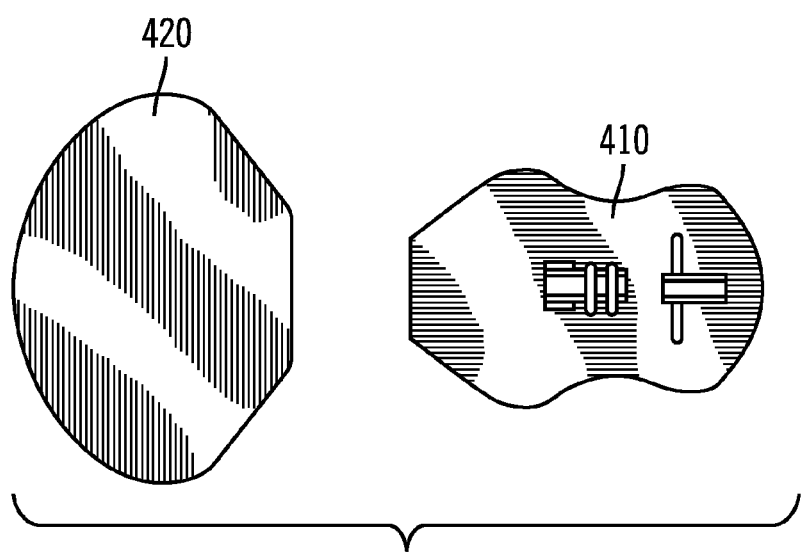

In accordance with another embodiment, the present invention may be implemented in a characteristic sensor system. Such system may include a characteristic monitor operationally coupled to a sensor set inserted into a patient's body to determine levels of a characteristic in the patient's body, such as blood glucose levels. FIGS. 4A and 4B illustrate a characteristic sensor system 400 comprising a subcutaneous sensor insertion set 410 and a telemetered characteristic monitor transmitter 420. Description of a telemetered characteristic sensor system may be found in commonly owned co-pending application Ser. No. 11/322,568 entitled "Telemetered Characteristic Monitor System and Method of Using the Same" filed on Dec. 30, 2005, which is incorporated by reference in its entirety. In a particular embodiment, the transmitter 420 and the sensor insertion set 410 are configured to directly connect with, and detach from, each other. FIG. 4A is a perspective view illustrating the transmitter 420 connected with the sensor set 410. FIG. 4B is a top view illustrating the transmitter 420 detached from the sensor set 410. The transmitter 420 communicates with a characteristic monitor 430 to transmit information detected by the sensor set 410. The monitor 430 utilizes the transmitted information to determine the characteristic reading of the patient. The monitor 430 may include a display 440 to display the results of the characteristic reading to the user.

Figure 5A:
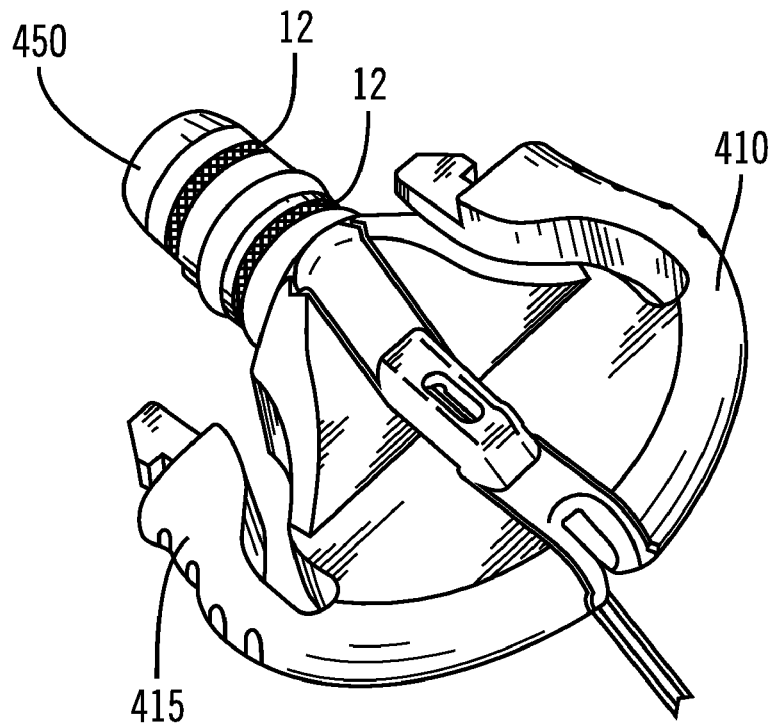
FIGS. 5A and 5B illustrate perspective views of a subcutaneous sensor insertion set having a colored marking in accordance with embodiments of the present invention.
Figure 6A:
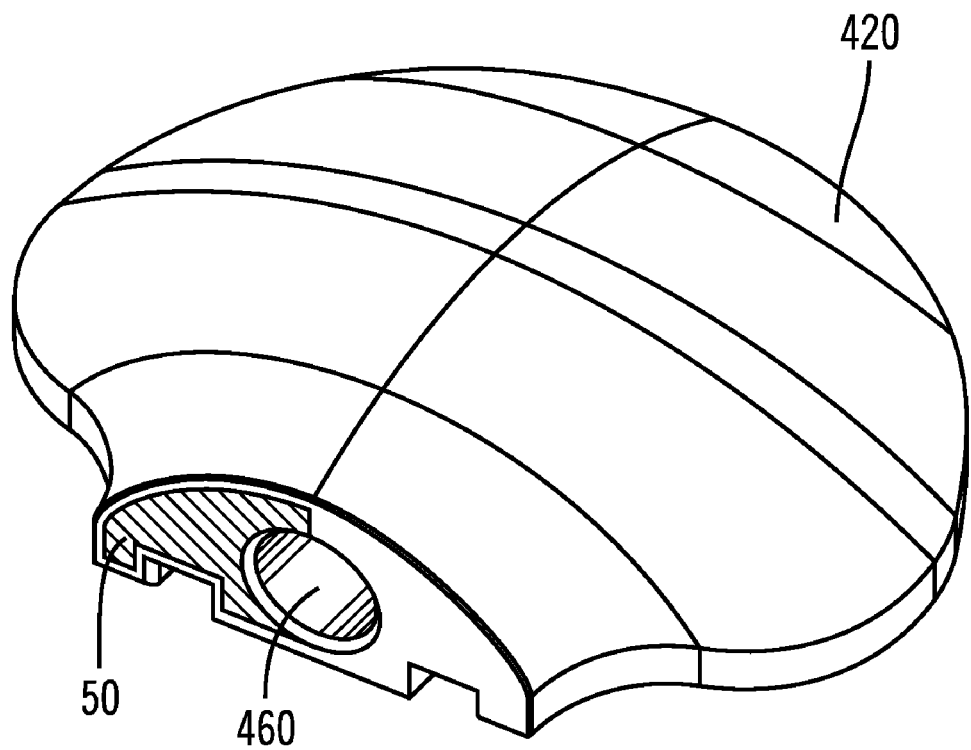
FIGS. 6A and 6B illustrate perspective views of a telemetered characteristic monitor transmitter having a window in accordance with embodiments of the present invention.
Figure 6B:
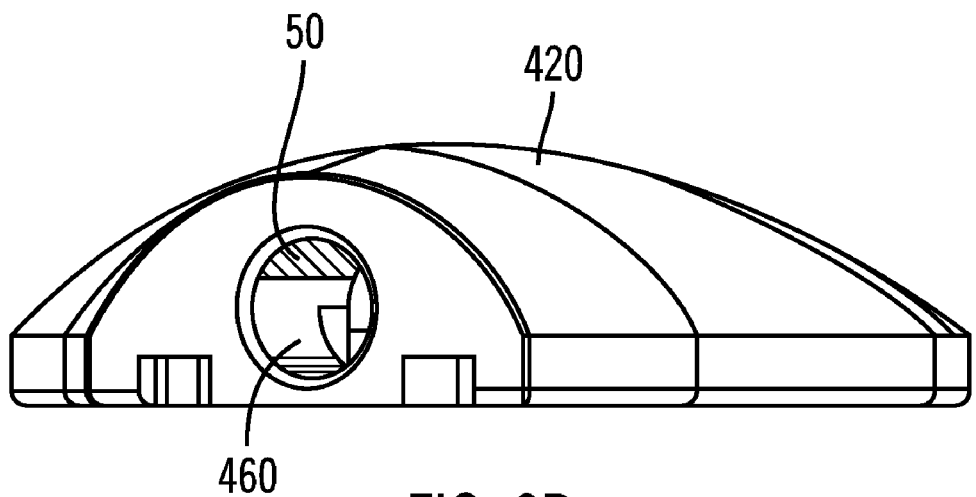

In one embodiment, the colored marking 12 may be located on the sensor set 410 and a light source and color sensor may be formed on, or within, a portion of the transmitter 420 that contacts a portion of the sensor set 410 having the colored marking 12 when the transmitter 420 and sensor set 410 are coupled to each other. For example, as shown in FIG. 5A, the colored marking 12 may be formed on a tubular portion 450 of the sensor set 410. Accordingly, a light source 30 and color sensor 32 may be formed within the transmitter 420. As shown in FIG. 6B, a window 50 may be formed on an inner wall of an interface 460 of the transmitter 420. Thus, when the sensor set 410 is operationally coupled to the transmitter 420 by inserting the tubular portion 450 into the interface 460, the light source 30 housed within the transmitter 420 can shine light on the colored marking 12 through the window 50. The sensor 32 housed within the transmitter 420 can also detect wavelengths reflected and/or refracted from the tubular portion 450 through the window 50. As such, when the light source shines light on the colored marking 12 and wavelengths reflected and/or refracted from the marking 12 are sensed by the color sensor, information related to the sensor set 410 or the monitored characteristic may be indicated to the monitor 430 according to a color of the marking 12. The color may be determined by a processor operatively coupled to the color sensor or the monitor 430. The processor may also ascertain the information from a transmitter memory or monitor memory according to the determined color. The information may include usage life of the sensor (e.g., 3 days, 6 days), an analyte being sensed (e.g, glucose, lactate, bacterial, viral, ph, oxygen, or the like), calibration data, alarm thresholds, lot number, or the like. The location, form and number of the colored markings 12 as shown in FIG. 5A is for illustrative purposes only. In accordance with the present invention, any number of colored markings may be placed, in any form, on any location of the tubular portion 450 or the sensor set 410 in general. Furthermore, the location, size and shape of the window 50 as shown in FIG. 6B is for illustrative purposes only. The window 50 may be formed at any inner wall portion of the interface 460, or on any surface of the transmitter 420, and may have any size and shape.

Figure 5B:
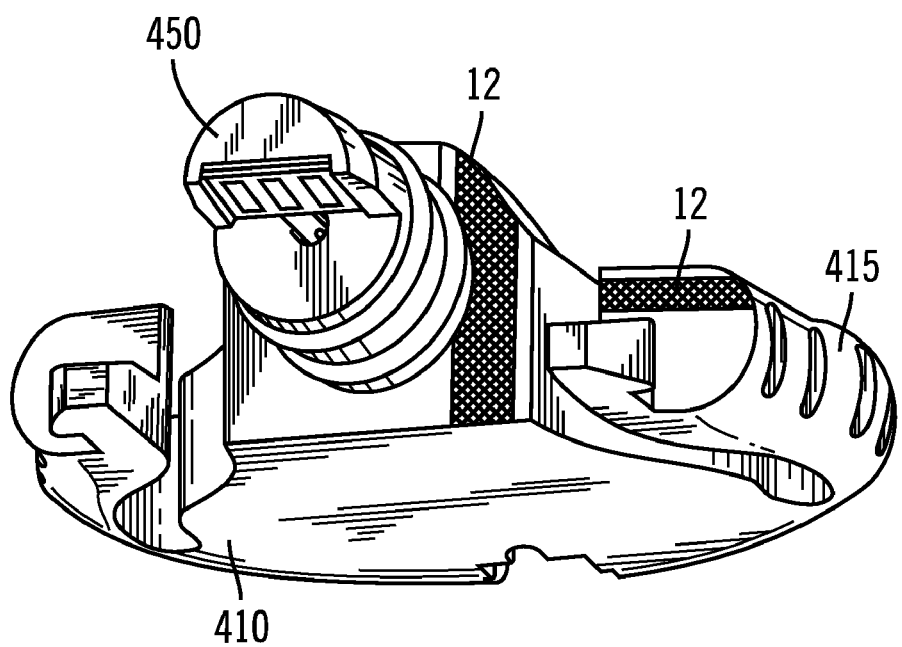

In another embodiment, as shown in FIG. 5B, the colored marking 12 may be formed on a rear wall surface of the sensor set 410 wherefrom the tubular portion 450 extends, or on a rear wall surface of a cantilevered latch arm 415. As shown in FIG. 6A, a window 50 may be formed on a front wall surface of the transmitter 420. Thus, when the sensor set 410 is coupled to the transmitter 420 by snap-fitting a latch tip of the latch arm 415 into a corresponding latch recess of the transmitter 420, the colored marking 12 of the sensor set 410 may be visible to the light source 30 and color sensor 32 of the transmitter 420 through the window 50. As such, as described above, when the light source shines light on the colored marking 12 and wavelengths reflected and/or refracted from the marking 12 are sensed by the color sensor, information related to the sensor set 410 or the monitored characteristic may be indicated to the monitor 430 according to a color of the marking 12. The location, form and number of the colored markings 12 as shown in FIG. 5B is for illustrative purposes only. In accordance with the present invention, any number of colored markings may be placed, in any form, on any surface of the sensor set 410. Furthermore, the location, size and shape of the window 50 as shown in FIG. 6A is for illustrative purposes only. The window 50 may be formed at any wall portion, or on any surface of the transmitter 420, and may have any size and shape.

The foregoing embodiments and advantages are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. In the claims, any means-plus-function clauses are intended to cover the structure described herein as performing the recited function and not only structural equivalents but also equivalent structures.

What is claimed is:

1. A characteristic monitor system for monitoring a characteristic of a user, the system comprising:
   a remote device;
   a sensor set supporting a sensor for producing a signal indicative of the characteristic of the user; at least one colored marking located on a surface of the sensor set for providing information related to the sensor set or the characteristic of the user; and
   a transmitter coupled to the sensor set for processing signals from the sensor set and transmitting the processed signals to the remote device,
   wherein the remote device utilizes the received processed signals to determine the characteristic of the user, the transmitter comprising:
   a light source for shining light on the at least one colored marking of the sensor set,
   a color sensor for detecting wavelengths reflected and/or refracted from the at least one colored marking due to the light shined on the at least one colored marking, and
   a processor operatively coupled to the color sensor for determining a color of the at least one colored marking from the detected wavelengths and ascertaining information related to the sensor set or the monitored characteristic corresponding to the determined color,
   wherein the transmitter further comprises a window through which the light source shines light on the at least one colored marking of the sensor set and the color sensor detects wavelengths reflected and/or refracted from the at least one colored marking, the window being formed on a front wall surface of the transmitter and the at least one colored marking is formed on a rear wall surface of the sensor set.

2. The system of claim 1, wherein the information comprises at least one of: usage life of the sensor; an analyte being sensed; calibration data; alarm thresholds; and lot number.

3. A characteristic monitor system for monitoring a characteristic of a user, the system comprising:
   a remote device;
   a sensor set supporting a sensor for producing a signal indicative of the characteristic of the user; at least one colored marking located on a surface of the sensor set for providing information related to the sensor set or the characteristic of the user; and
   a transmitter coupled to the sensor set for processing signals from the sensor set and transmitting the processed signals to the remote device,
   wherein the remote device utilizes the received processed signals to determine the characteristic of the user, the transmitter comprising:
   a light source for shining light on the at least one colored marking of the sensor set,
   a color sensor for detecting wavelengths reflected and/or refracted from the at least one colored marking due to the light shined on the at least one colored marking, and
   a processor operatively coupled to the color sensor for determining a color of the at least one colored marking from the detected wavelengths and ascertaining information related to the sensor set or the monitored characteristic corresponding to the determined color,
   wherein the transmitter further comprises a window through which the light source shines light on the at least one colored marking of the sensor set and the color sensor detects wavelengths reflected and/or refracted from the at least one colored marking, the window being formed on an inner wall surface of an interface of the transmitter.

4. The system of claim 3, wherein the at least one colored marking is formed on a portion of the sensor set that inserts into the interface when the sensor set is coupled to the transmitter.

5. A characteristic monitor system for monitoring a characteristic of a user, the system comprising:
   a sensor set supporting a sensor for producing a signal indicative of the characteristic of the user;
   at least one colored marking located on a surface of the sensor set for providing information related to the sensor set or the characteristic of the user; and
   a transmitter coupled to the sensor set for processing signals from the sensor set to determine the characteristic of the user, the transmitter comprising:
   a light source for shining light on the at least one colored marking of the sensor set, a color sensor for detecting wavelengths reflected and/or refracted from the at least one colored marking due to the light shined on the at least one colored marking,
   a window through which the light source shines light on the at least one colored marking of the sensor set and the color sensor detects wavelengths reflected and/or refracted from the at least one colored marking, and
   a processor operatively coupled to the color sensor for determining a color of the at least one colored marking from the detected wavelengths and ascertaining information related to the sensor set or the monitored characteristic corresponding to the determined color,
   wherein the window is formed on a front wall surface of the transmitter and the at least one colored marking is formed on a rear wall surface of the sensor set.

6. A characteristic monitor system for monitoring a characteristic of a user, the system comprising:

a sensor set supporting a sensor for producing a signal indicative of the characteristic of the user:

at least one colored marking located on a surface of the sensor set for providing information related to the sensor set or the characteristic of the user; and a transmitter coupled to the sensor set for processing signals from the sensor set to determine the characteristic of the user, the transmitter comprising:

a light source for shining light on the at least one colored marking of the sensor set, a color sensor for detecting wavelengths reflected and/or refracted from the at least one colored marking due to the light shined on the at least one colored marking, a window through which the light source shines light on the at least one colored marking of the sensor set and the color sensor detects wavelengths reflected and/or refracted from the at least one colored marking, and a processor operatively coupled to the color sensor for determining a color of the at least one colored marking from the detected wavelengths and ascertaining information related to the sensor set or the monitored characteristic corresponding to the determined color, wherein the window is formed on an inner wall surface of an interface of the transmitter.

7. The system of claim 6, wherein the at least one colored marking is formed on a portion of the sensor set that inserts into the interface when the sensor set is coupled to the transmitter.

8. The system of claim 6, wherein the information comprises at least one of: usage life of the sensor; an analyte being sensed; calibration data; alarm thresholds; and lot number.

9. A characteristic monitor system for monitoring a characteristic of a user, the system comprising:

a sensor set supporting a sensor for producing a signal indicative of the characteristic of the user;

at least one colored marking located on a surface of the sensor set for providing information related to the sensor set or the characteristic of the user; and a transmitter coupled to the sensor set for processing signals from the sensor set to determine the characteristic of the user, wherein the at least one colored marking is formed on a portion of the sensor set that inserts into the transmitter when the sensor set is coupled to the transmitter, the transmitter comprising:

a light source for shining light on the at least one colored marking of the sensor set, a color sensor for detecting wavelengths reflected and/or refracted from the at least one colored marking due to the light shined on the at least one colored marking, an interface for receiving the portion of the sensor set that inserts into the transmitter, a window formed on an inner wall surface of the interface through which the light source shines light on the at least one colored marking of the sensor set and the color sensor detects wavelengths reflected and/or refracted from the at least one colored marking, and a processor operatively coupled to the color sensor for determining a color of the at least one colored marking from the detected wavelengths and ascertaining information related to the sensor set or the monitored characteristic corresponding to the determined color.

10. The system of claim 9, wherein the information comprises at least one of: usage life of the sensor; an analyte being sensed; calibration data; alarm thresholds; and lot number.

11. A characteristic monitor system for monitoring a characteristic of a user, the system comprising:

a sensor set supporting a sensor for producing a signal indicative of the characteristic of the user;

at least one colored marking located on a rear wall surface of the sensor set for providing information related to the sensor set or the characteristic of the user; and a transmitter coupled to the sensor set for processing signals from the sensor set to determine the characteristic of the user, the transmitter comprising:

a light source for shining light on the at least one colored marking of the sensor set, a color sensor for detecting wavelengths reflected and/or refracted from the at least one colored marking due to the light shined on the at least one colored marking, a window formed on a front wall surface of the interface through which the light source shines light on the at least one colored marking of the sensor set and the color sensor detects wavelengths reflected and/or refracted from the at least one colored marking, and a processor operatively coupled to the color sensor for determining a color of the at least one colored marking from the detected wavelengths and ascertaining information related to the sensor set or the monitored characteristic corresponding to the determined color.

12. The system of claim 11, wherein the information comprises at least one of: usage life of the sensor; an analyte being sensed; calibration data; alarm thresholds; and lot number.

* * * * *